United States Patent
Kwak et al.

(10) Patent No.: US 9,107,602 B2
(45) Date of Patent: Aug. 18, 2015

(54) ADAPTIVE CLUTTER FILTERING IN AN ULTRASOUND SYSTEM

(75) Inventors: Han Kwak, Seoul (KR); Jae Keun Lee, Seoul (KR); Jong Sik Kim, Seoul (KR)

(73) Assignee: SAMSUNG MEDISON CO., LTD., Hongchun-Gun, Kangwon-Do (KR)

( * ) Notice: Subject to any disclaimer, the term of this patent is extended or adjusted under 35 U.S.C. 154(b) by 908 days.

(21) Appl. No.: 13/163,093

(22) Filed: Jun. 17, 2011

(65) Prior Publication Data

US 2011/0313292 A1 Dec. 22, 2011

(30) Foreign Application Priority Data

Jun. 17, 2010 (KR) .................. 10-2010-0057426

(51) Int. Cl.
- *A61B 5/02* (2006.01)
- *A61B 8/00* (2006.01)
- *A61B 8/06* (2006.01)
- *G01S 15/89* (2006.01)

(52) U.S. Cl.
CPC ............... *A61B 8/06* (2013.01); *G01S 15/8981* (2013.01)

(58) Field of Classification Search
USPC .......................................................... 600/453
See application file for complete search history.

(56) References Cited

U.S. PATENT DOCUMENTS

| | | | |
|---|---|---|---|
| 5,800,357 A | 9/1998 | Witt et al. | |
| 5,910,118 A | 6/1999 | Kanda et al. | |
| 2003/0073903 A1 | 4/2003 | Sato | |
| 2006/0055488 A1* | 3/2006 | Ten Dolle et al. | ............ 333/190 |
| 2008/0240448 A1* | 10/2008 | Gustafsson et al. | ............ 381/17 |
| 2009/0240153 A1* | 9/2009 | Kim | ............... 600/453 |

FOREIGN PATENT DOCUMENTS

| | | |
|---|---|---|
| EP | 0 316 200 A2 | 5/1989 |
| EP | 0 795 296 A1 | 9/1997 |
| EP | 2 103 954 A1 | 9/2009 |
| JP | 06-245932 A | 9/1994 |
| JP | 07-016227 A | 1/1995 |
| JP | 10-099333 A | 4/1998 |
| JP | 2003-250802 A | 9/2003 |
| JP | 2009-226218 A | 10/2009 |

(Continued)

OTHER PUBLICATIONS

Yoo, Y. M., et al., "Adaptive Clutter Filtering for Ultrasound Color Flow Imaging", Sep. 1, 2003, pp. 1311-1320, vol. 29 No. 9, Ultrasound in Medicine and Biology, New York, NY.

(Continued)

*Primary Examiner* — Tse Chen
*Assistant Examiner* — Patricia Park
(74) *Attorney, Agent, or Firm* — McDermott Will & Emery LLP

(57) ABSTRACT

Embodiments for adaptively performing clutter filtering upon in an ultrasound system are disclosed. In one embodiment, the ultrasound system includes: an ultrasound data acquisition unit configured to transmit ultrasound signals to a target object and receive ultrasound echoes reflected from the target object to thereby acquire ultrasound data; and a processing unit configured to form a Doppler signal corresponding to each of a plurality of pixels constructing a Doppler mode image based on the ultrasound data, as well as to adjust coefficients of a clutter filter based on characteristics of the Doppler signal for each of the pixels for performing clutter filtering upon the Doppler signal.

15 Claims, 4 Drawing Sheets

(56) References Cited

FOREIGN PATENT DOCUMENTS

| KR | 10-2000-0073096 A | 12/2000 |
|---|---|---|
| KR | 10-0352638 B | 8/2002 |
| WO | WO 99/58061 A1 | 11/1999 |

OTHER PUBLICATIONS

Hoeks, A. P. G. et al., "An Efficient Algorithm to Remove Low Frequency Doppler Signals in Digital Doppler Systems", Apr. 1, 1991, pp. 135-144, vol. 13 No. 2, Ultrasonic Imaging, Dynamedia Inc., Silver Spring, MD.

Extended European Search Report, issued in European Patent Application No. 11 170 018.3, dated Oct. 5, 2011.
European Office Communication issued in European Patent Application No. EP 11 170 018.3 dated Oct. 2, 2013.
Korean Office Action issued in Korean Patent Application No. KR 10-2010-0057426 dated Aug. 26, 2011.
S. Bjaerum et al., "Clutter Filter Design for Ultrasound Color Flow Imaging," IEEE Transactions on Ultrasonics, Ferroelectrics, and Frequency Control, vol. 49, No. 2, Feb. 2002, pp. 204-216.
Japanese Office Action issued in Japanese Patent Application No. 2011-134964 dated Mar. 3, 2015, with English Translation.

* cited by examiner

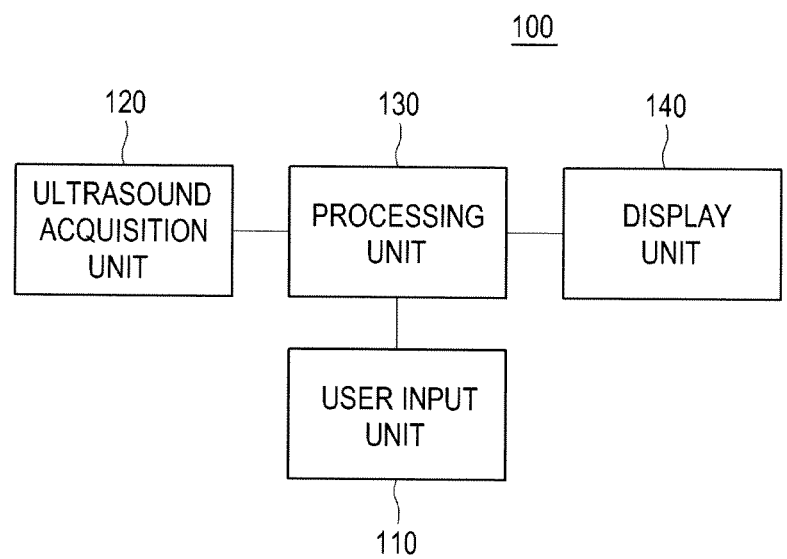
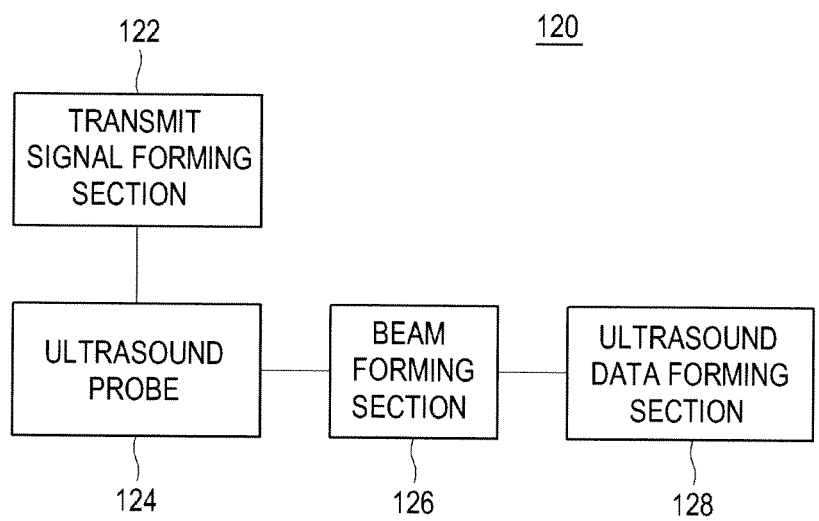

ADAPTIVE CLUTTER FILTERING IN AN ULTRASOUND SYSTEM

CROSS-REFERENCE TO RELATED APPLICATIONS

The present application claims priority from Korean Patent Application No. 10-2010-0057426 filed on Jun. 17, 2010, the entire subject matter of which is incorporated herein by reference.

TECHNICAL FIELD

The present disclosure generally relates to ultrasound image processing, and more particularly to adaptive clutter filtering in an ultrasound system.

BACKGROUND

An ultrasound system has been extensively used in the medical field due to its non-invasive and non-destructive nature. Modern high-performance ultrasound imaging diagnostic systems and techniques are commonly used to produce two-dimensional or three-dimensional ultrasound images of internal features of patients.

The ultrasound system transmits ultrasound signals to the target objects, receives echo signals reflected from the target objects and provides a color Doppler mode image of the target object based on the echo signals. In the color Doppler mode image, velocities of the target object (e.g., blood flow), which flows toward an ultrasound probe, are indicated in a first color (e.g., red), while velocities of the target object, which flows away from an ultrasound probe, are indicated in a second color (e.g., blue).

The signal received by the ultrasound probe is converted into a digital signal at a front end. The digital signal is receive-focused to thereby obtain a receive-focused signal. The band of the receive-focused signal is modulated by a mixer and then the receive-focused signal is appropriately decimated so that In-phase/Quadrature (IQ) signal is obtained. This IQ signal is referred to as a baseband IQ signal. The IQ signal may be expressed by the following equation.

$$X_{IQ}=C+F+N \quad (1)$$

wherein $X_{IQ}$ represents an IQ signal, C represents a clutter signal generated from a tissue, F represents a blood flow signal generated from blood flow, and N represents a noise signal generated from the system and exterior.

Essential information from Equation (1) is information on F, i.e., the blood flow signal. Color Doppler processing represents a process of extracting components on the blood flow signal from the IQ signal and processing the extracted components into data for display on a screen. Clutter filtering is an essential processing step in the color Doppler processing. The clutter filtering is performed to remove a low-band clutter signal from a Doppler signal to thereby extract only a blood flow signal and a noise signal. The filtered Doppler signal contains the blood flow signal and the noise, which are mixed with each other. The noise may be removed through signal processing. Then, the components on the blood flow signal are displayed on a screen.

Generally, the clutter signal is distributed at a low frequency band, whereas the blood flow signal is distributed at a high frequency band. Thus, a high pass filter should be designed to remove the clutter signal. However, the amplitude of the clutter signal is higher than that of the blood flow signal by 40-60 dB. As such, it is not easy to extract only the blood flow signal. Accordingly, a high performance of the high pass filter is required.

Further, since an effective clutter filtering may be limited due to a small ensemble number, various filtering techniques have been developed. The clutter filter may be classified into a finite impulse response (FIR), an infinite impulse response (IIR) and a Regression. In case of the IIR filter, various initializing techniques such as zero, step, exponential, projection, etc. have been developed to suppress the transient. The Regression-type filter is classified into a polynomial filter, a sinusoidal regression filter and the like.

Conventionally, a clutter filter is properly selected depending on the application of an ultrasound system and the clutter filtering is performed with only the selected clutter filter. In such a case, i.e., if an identical clutter filter is applied to entire regions within a region of interest, the quality of an ultrasound image may be degraded.

SUMMARY

Embodiments for adaptively performing clutter filtering in an ultrasound system are disclosed herein. In one embodiment, by way of non-limiting example, an ultrasound system comprises: an ultrasound data acquisition unit configured to transmit ultrasound signals to a target object and receive ultrasound echoes reflected from the target object to thereby acquire ultrasound data; and a processing unit configured to form a Doppler signal corresponding to each of a plurality of pixels constructing a Doppler mode image based on the ultrasound data, as well as to adjust coefficients of a clutter filter based on characteristics of the Doppler signal for each of the pixels for performing clutter filtering upon the Doppler signal.

In another embodiment, a method of adaptively performing clutter filtering, comprises: a) acquiring ultrasound data indicative of a target object; and b) forming a Doppler signal corresponding to each of a plurality of pixels constructing a Doppler mode image based on the ultrasound data; and c) adjusting coefficients of a clutter filter based on characteristics of the Doppler signal for each of the pixels for performing clutter filtering upon the Doppler signal.

In yet another embodiment, a computer-readable storage medium storing instructions that, when executed by a computer, cause the computer to provide a method of adaptively performing clutter filtering upon in an ultrasound system is provided, the method comprising: a) acquiring ultrasound data indicative of a target object; and b) forming a Doppler signal corresponding to each of a plurality of pixels constructing a Doppler mode image based on the ultrasound data; and c) adjusting coefficients of a clutter filter based on characteristics of the Doppler signal for each of the pixels for performing clutter filtering upon the Doppler signal.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 1 is a block diagram showing an illustrative embodiment of an ultrasound system.

FIG. 2 is a block diagram showing an illustrative embodiment of an ultrasound data acquisition unit.

DETAILED DESCRIPTION

Figure 3:
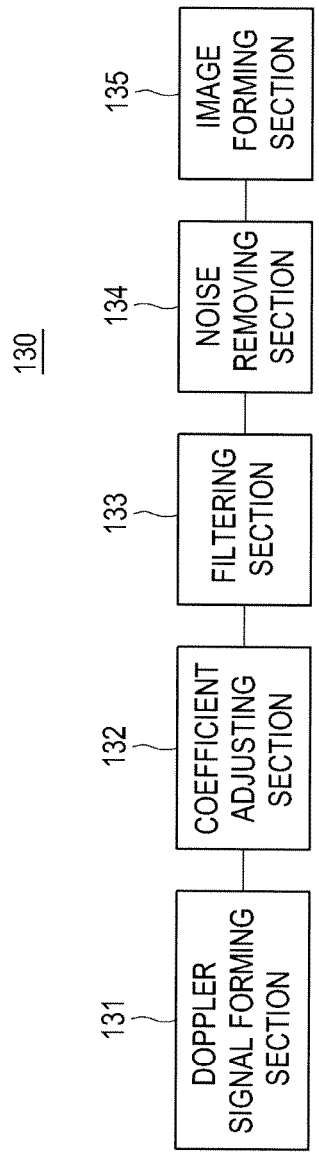
FIG. 3 is a block diagram showing an illustrative embodiment of a processing unit.

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure. The term "Doppler mode" described in the following embodiments includes a color Doppler mode, a spectral Doppler mode and the like.

Referring to FIG. 1, an ultrasound system constructed in accordance with one embodiment is shown therein. The ultrasound system 100 includes a user input unit 110, an ultrasound data acquisition unit 120, a processing unit 130 and a display unit 140.

The user input unit 110 receives a user request from a user. In one embodiment, the user request includes a first user request for setting a region of interest (ROI) on a brightness mode (B-mode) image. Also, the user request further includes a second user request for adjusting coefficients of a clutter filter to filter out a clutter signal from a Doppler signal for each of pixels constructing a Doppler mode image. The filter coefficients include a cutoff frequency, stopband attenuation and the like.

The ultrasound data acquisition unit 120 is configured to transmit ultrasound beams to a target object and receive ultrasound echoes reflected from the target object to thereby form ultrasound data representative of the target object. An operation of the ultrasound acquisition unit 120 will be described in detail by referring to FIG. 2.

FIG. 2 is a block diagram showing an illustrative embodiment of the ultrasound data acquisition unit 120. Referring to FIG. 2, the ultrasound data acquisition unit 120 may include a transmit (Tx) signal forming section 122. The Tx signal forming section 122 may generate a plurality of Tx signals and apply delays to the Tx signals. The delays of the Tx signals may be controlled according to an image mode such as a brightness mode, a Doppler mode and the like, which may be provided in the ultrasound system. In one embodiment, the Tx signals include first Tx signals for the brightness mode and second Tx signals for the Doppler mode.

The ultrasound data acquisition unit 120 may further include an ultrasound probe 124, which is coupled to the Tx signal forming section 122. The ultrasound probe 124 may include an array transducer containing a plurality of transducer elements for reciprocal conversion between electric signals and ultrasound signals. The ultrasound probe 124 may be configured to transmit ultrasound signals in response to the Tx signals. The ultrasound probe 124 may be further configured to receive ultrasound echoes reflected from the target object to thereby output receive signals. In one embodiment, the receive signals may include first receive signals obtained in response to the first Tx signals and second receive signals obtained in response to the second Tx signals.

The ultrasound data acquisition unit 120 may further include a beam forming section 126, which is coupled to the ultrasound probe 124. The beam forming section 126 may be configured to digitize the receive signals to obtain digital signals. The beam forming section 126 may apply delays to the digital signals in consideration of distances between the elements of the ultrasound probe 124 and focal points. Thereafter, the beam forming section 126 may sum the delayed digital signals to form receive-focused signals. In one embodiment, the beam forming section 126 may form a first receive-focused signal based on the first receive signals and a second receive-focused signal based on the second receive signals.

The ultrasound data acquisition unit 120 may further include an ultrasound data forming section 128, which is coupled to the beam forming section 126. The ultrasound data forming section 128 may be configured to form ultrasound data based on the receive-focused signals. In one embodiment, the ultrasound data forming section 128 may be configured to form first ultrasound data based on the first receive-focused signal. The first ultrasound data may include radio frequency data. However, the first ultrasound data may not be limited thereto. The ultrasound data forming section 128 may be configured to form second ultrasound data based on the second receive-focused signal. The second ultrasound data may include in-phase/quadrature data (i.e., ensemble data). However, the second ultrasound data may not be limited thereto.

Referring back to FIG. 1, the processing unit 130, which is coupled to the user input unit 110 and the ultrasound data acquisition unit 120, may be configured to form a Doppler signal based on the second ultrasound data. The processing unit 130 may be further configured to adaptively perform clutter filtering upon the Doppler signal for each of pixels constructing a Doppler mode image to filter out the clutter signal from the Doppler signal. The processing unit 130 may form a Doppler mode image based on the Doppler signal with the clutter signal filtered out. Also, the processing unit 130 may be configured to form a B-mode image based on the first ultrasound data.

FIG. 3 is a block diagram showing an illustrative embodiment of a processing unit. Referring to FIG. 3, the processing unit 130 includes a Doppler signal forming section 131, a coefficient adjusting section 132, a filtering section 133, a noise removing section 134 and an image forming section 135.

The Doppler signal forming section 131 is configured to perform signal processing such as decimation, modulation and the like, upon the second ultrasound data, which are provided from the ultrasound data acquisition unit 120, to thereby form a Doppler signal corresponding to a plurality of pixels of a Doppler mode image. The Doppler signal includes a blood flow signal caused by the blood flow, a clutter signal caused by the motion of tissues such as cardiac wall, cardiac valve and the like, and a noise signal.

The coefficient adjusting section 132 may be configured to analyze the Doppler signal, which is provided from the Doppler signal forming section 131, to adjust coefficients of a clutter filter for clutter filtering upon the Doppler signal for each pixel.

The blood flow signal is a signal necessary for forming the Doppler mode image so that the clutter signal and the noise signal have to be removed from the Doppler signal. Amplitude has an order wherein clutter signal>blood flow signal>the noise signal. To efficiently remove the clutter signal, stopband attenuation and stopband width, which are coefficients of the clutter filter, should be appropriately determined. In one embodiment, the stopband attenuation and the stopband width may be determined according to characteristics of the clutter signal. The stopband width is determined by a bandwidth of the clutter signal and the stopband attenuation is determined by amplitude of the clutter signal. However, the stopband attenuation and the stopband width have a trade off in relation. That is, if the stopband attenuation is increased, then the stopband width is decreased. However, if the stopband attenuation is decreased, then the stopband width is increased.

Figure 4:
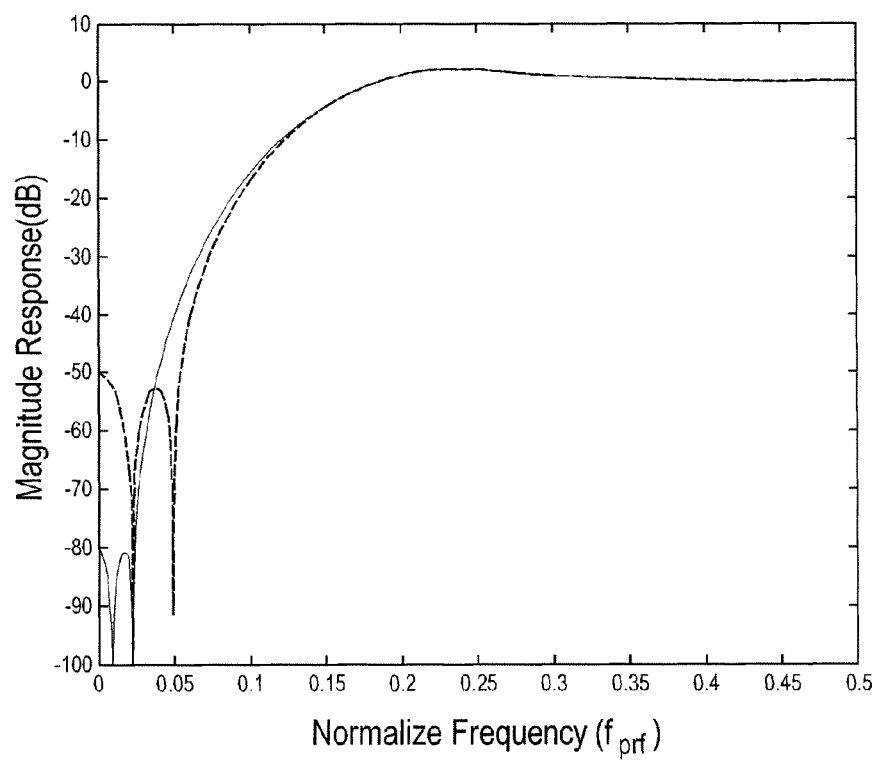
FIG. 4 is a graph showing a relationship between stopband attenuation and stopband width in a clutter filter.

FIG. 4 is a graph showing a relationship between the stopband attenuation and the stopband width in the clutter filter. As shown in FIG. 4, two curved lines represent frequency responses of different clutter filters having the same cutoff frequency of 0.16 pulse repetition frequency (prf). A solid line represents a frequency response of a clutter filter having stopband attenuation of 80 dB and a stopband width of 0.025 prf. Further, a dotted line represents a frequency response of a clutter filter having stop band attenuation of 50 dB and a stopband width of 0.055 prf.

Also, determining the cutoff frequency, which is another filter coefficient, is an essential process in designing the clutter filter. If the cutoff frequency is relatively low, then a blood flow signal corresponding to a slow speed may be preserved well. On the other hand, if the cutoff frequency is relatively high, then a wider stopband width may be secured while the blood flow signal corresponding to the slow speed is attenuated. This is so that clutter filter performance for removing the clutter signal may be improved. Thus, it is required to appropriately determine the cutoff frequency during the clutter filtering process.

Figure 5:
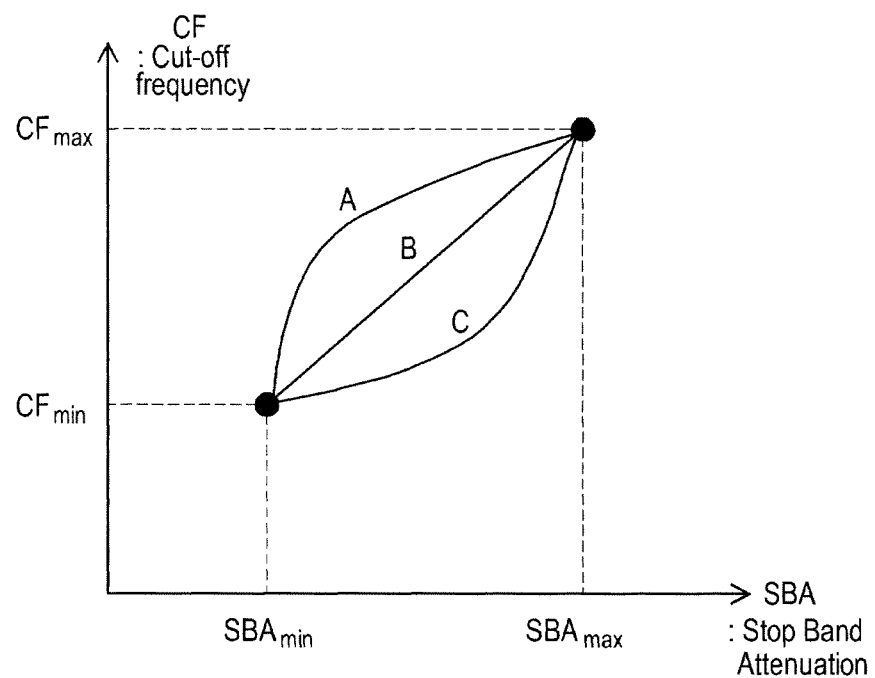
FIG. 5 is a graph showing a relationship between cutoff frequency and stopband attenuation for setting coefficients of a clutter filter.

FIG. 5 is a graph showing a relationship between a cutoff frequency and stopband attenuation for determining coefficients of the clutter filter. The stopband attenuation is an independent variable and the cutoff frequency is a dependent variable determined according to the stopband attenuation. The coefficient adjusting section 132 is configured to determine the cutoff frequency and the stopband attenuation of the clutter filter as the following process.

The coefficient adjusting section 132 is configured to determine an upper limit and a lower limit of a threshold of the cutoff frequency in consideration of a range for removing the clutter signal. In one embodiment, the coefficient adjusting section 132 is configured to determine a maximum cutoff frequency $CF_{max}$ for maximally removing the clutter signal as well as to determine a minimum cutoff frequency $CF_{min}$ for minimally removing the clutter signal to show the blood flow of a relative slow speed, which is desired to observe, in the Doppler mode image, even if a large amount of the clutter signal remains. The maximum cutoff frequency $CF_{max}$ represents the upper limit of the threshold of the cutoff frequency and the minimum cutoff frequency $CF_{min}$ represents the lower limit of the threshold.

In one embodiment, a velocity v of the blood flow may be computed by the following equation.

$$v = \frac{c}{2\cos\theta} \frac{f_d}{f_o} \quad (2)$$

wherein θ represents an angle between an ultrasound beam and a flowing direction of the blood flow, c is an acoustic velocity, $f_d$ represent a Doppler shift frequency and $f_o$ represents a transmit frequency.

Assuming that the cutoff frequency is $CF_o$, a detectable velocity of the blood flow may be computed as the following equation.

$$v = \frac{c}{2\cos\theta} \frac{CF_o}{f_o} \quad (3)$$

Thus, if the minimum velocity $v_{min}$ of the blood flow to be detected is determined, then the minimum cutoff frequency $CF_{min}$ may be computed as the following equation.

$$CF_{min} = 2\cos\theta \cdot f_o \cdot \frac{v_{min}}{c} \quad (4)$$

Further, as described above, the maximum cutoff frequency $CF_{max}$ may be determined to maximally remove the clutter signal based on Doppler signal distribution on a frequency domain. Also, the maximum cutoff frequency $CF_{min}$ may be empirically determined by considering components on the clutter signal.

The coefficient adjusting section 132 is further configured to determine an upper limit and a lower limit of a threshold of the stopband attenuation according to a power of the Doppler signal. In one embodiment, the coefficient adjusting section 132 is configured to compute a power of the Doppler signal for each pixel. The coefficient adjusting section 132 is also configured to determine a maximum power as maximum stopband attenuation $SBA_{max}$ and a minimum power as minimum stopband attenuation $SBA_{min}$. The coefficient adjusting section 132 is configured to determine the maximum stopband attenuation $SBA_{max}$ as an upper limit of the threshold of the stopband attenuation and to determine the minimum stopband attenuation $SBA_{min}$ as a lower limit of the threshold of the stopband attenuation.

Further, the coefficient adjusting section 132 is configured to determine first coordinates and second coordinates on a coordinate system associating the cutoff frequency with the stopband attenuation. The first coordinates are determined by the lower limit of the threshold of the stopband attenuation and the lower limit of the threshold of the cutoff frequency, while the second coordinates are determined by the upper limit of the threshold of the stopband attenuation and the upper limit of the threshold of the cutoff frequency.

The coefficient adjusting section 132 is further configured to set a path between first and second coordinates ($SBA_{min}$, $CF_{min}$) and ($SBA_{max}$, $CF_{max}$). Referring to FIG. 5, if the path is set like path A, then the blood flow of weak amplitude may be more clearly indicated while the performance of removing the clutter signal is degraded. If the path is set like path C, then a high performance of removing the clutter signal is expected. However, the blood flow signal of weak amplitude may be attenuated so that loss of information on the blood flow may be increased. Thus, an appropriate path may be close to path B at which the cutoff frequency and the stopband attenuation are proportional to each other. As for the path B, the stopband width may be a constant form at each cutoff frequency. Also, a more appropriate path may be set by using empirical methods.

The coefficient adjusting section 132 is configured to set the stopband attenuation for each pixel according to amplitude of the clutter signal contained in the Doppler signal, which is provided from the Doppler signal forming section 131. The coefficient adjusting section 132 is configured to compute the cutoff frequency for each pixel corresponding to the stopband attenuation for each pixel based on the proportional path set between the first coordinates ($SBA_{min}$, $CF_{min}$) and the second coordinates ($SBA_{max}$, $CF_{max}$). The coefficient adjusting section 132 is configured to adjust the cutoff frequency of the clutter filter based on the computed cutoff frequencies.

In one embodiment, the coefficient adjusting section 132 may be configured to be at least one of the filter coefficients of the clutter filter such as cutoff frequency and stopband attenuation in response to the second user request, which is provided by the user input unit 110.

The filtering section 133 is configured to perform clutter filtering upon the Doppler signal for each pixel by using the stopband attenuation and the cutoff frequency, which have been adjusted for each pixel in the coefficient adjusting section 132, to remove the clutter signal therefrom.

The noise removing section 134 is configured to set a predetermined power threshold to remove a noise signal from the Doppler signal in which the clutter signal has been filtered out. In such a case, if the filtering section 133 is configured to decrease the amplitude of the clutter signal instead of completely removing the clutter signal during the clutter filter, then the clutter signal may be removed together with the noise signal in the noise removing section 134.

The image forming section 135 is configured to form a Doppler mode image by using the Doppler signal in which the clutter signal and the noise signal have been removed. The image forming section 135 may be configured to perform various processing such as scan conversion and the like to form the Doppler mode image.

Referring back to FIG. 1, the display unit 140, which is coupled to the processing unit 130, is configured to display the Doppler mode image. The display unit 140 may include at least one of a cathode ray tube display, a liquid crystal display, an organic light emit diode display and the like.

In another embodiment, there is provided a computer-readable storage medium storing instructions that, when executed by a computer, cause the computer to provide a method of spatially compounding ultrasound images based on a plurality of ultrasound frame data sets acquired from a target object and at different steering angles of scan lines in an ultrasound system, the method comprising: setting a plurality of masks corresponding to the respective frames based on the plurality of ultrasound frame date sets for removing seam artifact to form a plurality of mask images corresponding to the respective frames; forming a plurality of ultrasound images corresponding to the plurality of frames based on the plurality of frame data sets; and spatially compounding the plurality of ultrasound image based on the plurality of mask images to form an ultrasound spatial compound image.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
a probe configured to transmit ultrasound signals to a target object and receive ultrasound echoes reflected from the target object to thereby acquire ultrasound data; and
a processing unit connected to the probe and configured to:
form a Doppler signal corresponding to each of a plurality of pixels constructing a Doppler mode image based on the ultrasound data,
adjust coefficients of a clutter filter based on characteristics of the Doppler signal for each of the pixels for performing clutter filtering upon the Doppler signal, the coefficients including a cutoff frequency and stopband attenuation,
determine minimum and maximum cutoff frequencies and minimum and maximum stopband attenuations based on the characteristic of the Doppler signal,
determine, on a coordinate system associating the cutoff frequency with the stopband attenuation, a first coordinate having the minimum cutoff frequency and the minimum stopband attenuation and a second coordinate having the maximum cutoff frequency and the maximum stopband attenuation,
determine a path connecting the first coordinate and the second coordinate, and
set a particular stopband attenuation and a particular cutoff frequency for a particular pixel according to an amplitude of a clutter signal contained in the Doppler signal and the path connecting the first coordinate and the second coordinate.

2. The ultrasound system of claim 1, wherein the processing unit includes:
a coefficient adjusting section configured to analyze the characteristics of the Doppler signal for each of the pixels to adjust the coefficients of the clutter filter;
a filtering section configured to perform the clutter filtering upon the Doppler signal for each of the pixels by using the adjusted coefficients to remove the clutter signal from the Doppler signal; and
a noise removing section configured to set a predetermined power threshold to remove a noise signal from the Doppler signal with the clutter signal filtered out.

3. The ultrasound system of claim 2, wherein the coefficient adjusting section is configured to:
set the minimum and the maximum cutoff frequencies based on a range for removing the clutter signal, and
determine the minimum and the maximum stopband attenuations based on a power of the Doppler signal.

4. The ultrasound system of claim 3, wherein the coefficient adjusting section is configured to set a maximum power of the Doppler signal as the maximum stopband attenuation and a minimum power of the Doppler signal as the minimum stopband attenuation.

5. The ultrasound system of claim 4, wherein:
the coefficient adjusting section is configured to determine the path connecting the first coordinate and the second coordinate to be a proportional path between the first and second coordinates, and
the stopband attenuation is an independent variable and the cutoff frequency is a dependent variable.

6. The ultrasound system of claim 5, wherein the processing unit is configured to determine the particular stopband attenuation for the particular pixel based on the amplitude of the clutter signal and to determine all the particular cutoff frequency corresponding to the determined particular stopband attenuation on the path connecting the first coordinate and the second coordinate to adjust the cutoff frequency of the clutter filter.

7. The ultrasound system of claim 6, further comprising a user input unit connected to the probe and configured to receive a user request for adjusting the stopband attenuation and the cutoff frequency, wherein the coefficient adjusting section is configured to adjust the adjusted stopband attenuation and the cutoff frequency in response to the user request.

8. A method of adaptively performing clutter filtering, comprising steps of:
   a) acquiring ultrasound data indicative of a target object; and
   b) forming a Doppler signal corresponding to each of a plurality of pixels constructing a Doppler mode image based on the ultrasound data; and
   c) adjusting coefficients of a clutter filter based on characteristics of the Doppler signal for each of the pixels for performing clutter filtering upon the Doppler signal, the coefficients including a cutoff frequency and stopband attenuation,
   wherein the step c) comprises:
   determining minimum and maximum cutoff frequencies and minimum and maximum stopband attenuations based on the characteristics of the Doppler signal,
   determining, on a coordinate system associating the cutoff frequency with the stopband attenuation, a first coordinate having the minimum cutoff frequency and the minimum stopband attenuation and a second coordinate having the maximum cutoff frequency and the maximum stopband attenuation, and
   determining a path connection the first coordinate and the second coordinate,
   setting a particular stopband attenuation and a particular cutoff frequency for a particular pixel according to an amplitude of a clutter signal contained in the Doppler signal and the path connecting the first coordinate and the second coordinate.

9. The method of claim 8, wherein the step c) includes:
   c1) analyzing the characteristics of the Doppler signal for each of the pixels to adjust the coefficients of the clutter filter;
   c2) performing the clutter filtering upon the Doppler signal for each of the pixels by using the adjusted coefficients to remove the clutter signal from the Doppler signal; and
   c3) setting a predetermined power threshold to remove a noise signal from the Doppler signal with the clutter signal filtered out.

10. The method of claim 9, wherein the step c1) includes:
    determining the minimum and the maximum cutoff frequencies based on a range for removing the clutter signal; and
    determining the minimum and the maximum stopband attenuations based on a power of the Doppler signal.

11. The method of claim 10, wherein the step c1) includes:
    determining a maximum power of the Doppler signal as the maximum stopband attenuation; and
    determining a minimum power of the Doppler signal as the minimum stopband attenuation.

12. The method of claim 11, wherein the step c1) further includes:
    determining the path connecting the first coordinate and the second coordinate to be a proportional path between the first and second coordinates,
    wherein the stopband attenuation is an independent variable and the cutoff frequency is a dependent variable.

13. The method of claim 12, wherein the step c) includes:
    determining the particular stopband attenuation for the particular pixel based on the amplitude of the clutter signal; and
    determining all the particular cutoff frequency corresponding to the determined stopband attenuation on the path connecting the first coordinate and the second coordinate to adjust the cutoff frequency of the clutter filter.

14. The method of claim 13, further comprising:
    receiving a user request for adjusting the stopband attenuation and the cutoff frequency; and
    adjusting the adjusted stopband attenuation and the cutoff frequency in response to the user request.

15. A non-statutory computer-readable storage medium storing instructions that, when executed by a computer, cause the computer to provide the method of adaptively performing clutter filtering upon in an ultrasound system, the method comprising claim 8.

* * * * *